United States Patent [19]

Chow et al.

[11] Patent Number: 4,508,857
[45] Date of Patent: Apr. 2, 1985

[54] COLOR-STABILIZED AROYL CHLORIDE COMPOSITIONS

[75] Inventors: Richard H. Chow, Williamsville; Emil J. Geering, Grand Island, both of N.Y.

[73] Assignee: Occidental Chemical Corporation, Niagara Falls, N.Y.

[21] Appl. No.: 523,238

[22] Filed: Aug. 15, 1983

[51] Int. Cl.$^3$ ............................................. C07C 51/64
[52] U.S. Cl. ................................................ 260/544 D
[58] Field of Search ..................................... 260/544 D

[56] References Cited

U.S. PATENT DOCUMENTS 3,869,485  3/1975  DeLong ........................ 260/544 D
4,104,300  8/1978  Zoche et al. .................. 260/544 D
4,294,777  10/1981 Bockmann et al. ............ 260/544 D

OTHER PUBLICATIONS

Hurd et al., *Journal of the American Chemical Society*, vol. 54, p. 2436, (Jun. 1932).
Zabicky, *The Chemistry of Amides*, Interscience Pub., London, (1970) pp. 107–108.
Wagner et al., *Synthetic Organic Chemistry*, Wiley, New York, (1953) p. 576.
Roberts et al., *Basic Principals of Organic Chemistry*, 2nd ed., W. A. Benjamin, Inc. (1977) p. 1183.

*Primary Examiner*—Natalie Trousof
*Assistant Examiner*—Bruce D. Gray
*Attorney, Agent, or Firm*—James F. Tao; Arthur S. Cookfair

[57] ABSTRACT

Aroyl chlorides are stabilized against discoloration by addition thereto of about 0.00001 to about 5.0% by weight of methanamide (formamide).

7 Claims, No Drawings

COLOR-STABILIZED AROYL CHLORIDE COMPOSITIONS

BACKGROUND OF THE INVENTION

Field of the Invention

This invention relates to color-stabilized aroyl chloride compositions and to a method for improving the color and/or color stability of aroyl chloride compositions.

Aroyl chlorides, such as benzoyl chloride, are used commercially in the manufacture of dye intermeidates and of peroxides, such as benzoyl peroxide.

Aroyl chlorides are known to exhibit an undesireable tendency to become discolored during storage. Benzoyl chloride, for example is a colorless liquid, and in commercial form is typically characterized by a color specification of less than 25 APHA. (APHA denotes a color unit system based on a visual comparison of a sample with standardized aqueous solution of potassium chloroplatinate and cobaltous chloride. The system is described in detail in Standard Methods for the Examination of Water and Wastewater, 15th ed., American Public Health Association, New York, 1981, p. 60–63). Frequently, while in storage or shipment in drums, trailers, tank cars and the like, benzoyl chloride will develop an undesireable color. Although the specific cause of discoloration is uncertain, it is considered that it may be related to the presence of iron or other metal contaminents in the aroyl chloride. Since the off-color material is generally unacceptable, it is often necessary to return and re-distill such material. The additional transportation, handling, and re-distillation may add substantially to the overall cost of the acid chloride. It will be apparent that a need exists for a simple inexpensive method to treat off-color material on-site, and thus eliminate the transportation and other costs associated with return and re-distillation. Furthermore, a need exists for a simple, inexpensive method for the stabilization of aroyl chlorides, to prevent discoloration during storage.

Material Information Disclosure Statement

U.S. Pat. No. 4,294,777 discloses the stabilization of aromatic carboxylic acid chlorides against discoloration by addition thereto of a color stabilizer. The various color stabilizers disclosed include, for example, acetone, methyl ethyl ketone, diethyl ketone, benzaldehyde, acetophenone, ethyl acetoacetate, acrylic acid ethyl ester, methacrylic acid methyl ester, crotonic acid, vinyl acetate, maleic acid, maleic acid diethyl ester, fumaric acid diethyl ester, dicyclopentadiene, e-caprolactam, styrene, methyl vinyl ketone, acrolein, cyclohexene, ally chloride, cinnamic acid, allyl alcohol, acetaldehyde, methyl phosphite, triphenylphosphine, phosphorus trichloride, arsenic trichloride, methacrylic acid amide and cyclohexanone and others.

U.S. Pat. No. 4,104,300 discloses the removal of molybdenum catalyst residues from carboxylic acid chlorides by treatment with a complexing agent, prior to distillation. A wide variety of complexing agents are disclosed, including, for example, benzamide and e-caprolactam.

SUMMARY OF THE INVENTION

In accordance with this invention there is provided an improved, colorstabilized aroyl chloride composition comprising an aroyl chloride containing about 0.00001 to about 5.0, and preferably about 0.01 to about 3.0 percent by weight of methanamide.

Aroyl chlorides that may be stabilized in accordance with this invention are of the formula

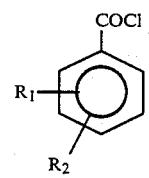

wherein $R_1$ and $R_2$ are independently selected from the group consisting of hydrogen, halogen, alkyl and alkoxy.

Suitable halogen substituents include fluorine, chlorine and bromine and most preferably chlorine.

Suitable alkyl and alkoxy groups include those having up to 10 carbon atoms and most preferably up to 4 carbon atoms, for example alkyl radicals such as methyl, ethyl, n-propyl, iso-propyl, n-butyl, iso-butyl, tert-butyl, n-pentyl, iso-pentyl, 2-methylpentyl, 3-methylpentyl, n-hexyl, n-heptyl, n-octyl, iso-octyl, n-nonyl, n-decyl and cyclohexyl, preferably methyl, ethyl, n-propyl, iso-propyl, n-butyl, iso-butyl and tert-butyl; and alkoxy radicals such as methoxy, ethoxy, propoxy, butoxy, pentyloxy and hexyloxy, preferably methoxy and ethoxy.

Aroyl chloride which may be color-stabilized in accordance with this invention, include for example, benzoyl chloride, o-toluic acid chloride, p-toluic acid chloride, 1-chlorobenzoyl chloride, 3-chlorobenzoyl chloride, 4-chlorobenzoyl chloride, 2,4-dichlorobenzoyl chloride, and anisic acid chloride.

The following specific details and examples are provided to further illustrate this invention, the advantages thereof, and the manner in which it may be carried out. It will be understood, however, that the specific details set forth are for purpose of illustration and are not to be construed as a limitation on the invention. In the examples, unless otherwise indicated, all parts and percentages are by weight and all temperatures are in degrees Celsius.

DETAILED DESCRIPTION OF THE INVENTION

The improved aroyl chloride compositions of this invention include, in a preferred embodiment, benzoyl chloride, containing about 0.00001 to about 5.0 percent, and most preferably about 0.01 to about 3.0 percent methanamide.

EXAMPLE I

A sample of discolored benzoyl chloride was examined using spectrophotometric analysis techniques and found to have a color number of 620 APHA. One microliter of methanamide was added to one liter of the discolored benzoyl chloride and the mixture was stirred and maintained at room temperature (20°–22° C.) for about 16 hours. Spectrophotometric analysis of the mixture indicated a color of 35 APHA. A subsequent addition of 2 microliters of formamide to the one liter sample of benzoyl chloride resulted in no further color change.

The addition of methanamide, in accordance with this invention, is particularly effective in the color-stabilization of benzoyl chloride. Moreover, it has been found, surprisingly, that benzoyl chloride, containing about 0.0001 to about 5.0 percent by weight methanamide, is particularly advantageous as a reactant in the preparation of benzoyl peroxide.

In a typical commercial process for manufacturing benzoyl peroxide from a reaction charge consisting primarily of aqueous sodium hydroxide, aqueous hydrogen peroxide and benzoyl chloride, the benzoyl peroxide is formed as particles, typically of about one to five millimeters in diameter. The product is then separated from the reaction mixture by filtration or centrifugation or a combination of these techniques, and then washed with water until it is free of salts, by-products and unchanged reagents. This separation and washing of product is facilitated if no product particles substantially smaller than the typical size are formed.

Benzoyl chloride containing 0.03 percent by weight methanamide was employed in a commercial process for the manufacture of benzoyl peroxide and the process was compared to similar processes utilizing benzoyl chloride containing no methanamide. In the process utilizing benzoyl chloride containing methanamide, several advantages were observed. The surface characteristics of the benzoyl peroxide particles formed was improved. The occurrence of surface pits or irregular shapes was minimized. The particles formed were more uniform in size. The amount of substantially smaller particles was reduced, with the result that the filter screens were not clogged by fine particles; wash water moved through more readily, thereby increasing the efficiency of each wash. The final centrifuge spin time was shortened by 20 percent because wash water could be released faster from the product matrix. The final washed and dewatered product was not subject to the formation of lumps. The formation of lumps is common in benzoyl peroxide products having high incidence of fine particles and irregularly shaped particles.

A further advantage of using benzoyl chloride containing methanamide was indicated by the improved processability of the resulting benzoyl peroxide into paste with solvent plasticizers. Unreacted benzoyl chloride was not stripped in the benzoyl peroxide particles as noted by the absence of benzoyl chloride odor when the particles were plasticized. The absence of benzoyl chloride is an indication of an improved reaction yield or efficiency. In addition, the break-down time of plasticization with solvents of the benzoyl peroxide was shortened, indicating a lack of impurities such as benzoic acid, sodium benzoate and benzaldehyde, which are not soluble.

What is claimed is:

1. An aroyl chloride composition comprising an aroyl chloride of the formula

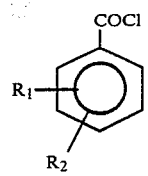

wherein $R_1$ and $R_2$ are independently selected from the group consisting of hydrogen, halogen, alkyl and alkoxy containing about 0.00001 to about 5.0 percent by weight of methanamide.

2. A composition according to claim 1 wherein the aroyl chloride is benzoyl chloride.

3. A composition according to claim 1 wherein methanamide is present in an amount of about 0.01 to about 3.0 percent by weight.

4. A composition according to claim 2 wherein methanamide is present in an amount of about 0.01 to about 3.0 percent by weight.

5. A method for color-stabilizing an aroyl chloride of the formula

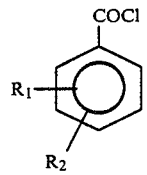

wherein $R_1$ and $R_2$ are independently selected from the group consisting of hydrogen, halogen, alkyl, and alkoxy, which comprises adding thereto about 0.0001 to about 5.0 percent by weight of methanamide.

6. A method according to claim 5, wherein the aroyl chloride is benzoyl chloride.

7. A method according to claim 6 wherein methanamide is added in an amount of about 0.01 to about 3.0 percent by weight.

* * * * *